United States Patent [19]
Reynolds

[11] Patent Number: 5,755,902
[45] Date of Patent: May 26, 1998

[54] METHOD AND APPARATUS FOR PRODUCING A COMPOSITE WEB HAVING TRANSVERSE STRETCH

[75] Inventor: Gary Mack Reynolds, Neenah, Wis.

[73] Assignee: Kimberly Clark Corporation, Neenah, Wis.

[21] Appl. No.: 760,552

[22] Filed: Dec. 5, 1996

[51] Int. Cl.$^6$ .......................... A61F 13/15; B32B 31/00
[52] U.S. Cl. .................. 156/73.1; 156/164; 156/210; 156/229; 156/292; 156/462; 156/472; 156/494; 156/496
[58] Field of Search .................. 156/160, 163, 156/164, 205, 210, 229, 206, 462, 471, 472, 474, 494, 495, 496, 73.1, 292, 285

[56] References Cited

U.S. PATENT DOCUMENTS

| | | |
|---|---|---|
| 4,240,866 | 12/1980 | Rega . |
| 4,259,220 | 3/1981 | Bunnelle et al. . |
| 4,285,747 | 8/1981 | Rega . |
| 4,379,016 | 4/1983 | Stemmler et al. ............. 156/205 |
| 4,397,704 | 8/1983 | Frick ........................ 156/472 X |
| 4,418,123 | 11/1983 | Bunnelle et al. ............ 156/164 |
| 4,488,923 | 12/1984 | Pieniak ...................... 156/229 X |
| 4,543,099 | 9/1985 | Bunnelle et al. . |
| 4,618,384 | 10/1986 | Sabee ........................ 156/205 |
| 4,842,666 | 6/1989 | Werenicz . |
| 4,968,313 | 11/1990 | Sabee ........................ 156/164 X |
| 5,171,388 | 12/1992 | Hoffman et al. ............. 156/210 X |
| 5,451,219 | 9/1995 | Suzuki et al. . |

*Primary Examiner*—Jeff H. Aftergut
*Attorney, Agent, or Firm*—Thomas D. Wilhelm; Brian R. Tumm

[57] ABSTRACT

This invention relates to apparatus and methods for fabricating a composite web having transverse stretch. In one embodiment a forming plow forms at least one groove in a first web of material. An applicator roll applies a second web of transversely stretchable material to the first web while maintaining a facing portion of the second web in facing relationship with, and spaced from, the portion of the first web formed in the groove. Urging apparatus, such as a push roll having an axis, can intermittently urge the second web into the groove and thereby into surface-to-surface relationship with the first web over substantially the entirety of the facing portion of the second web. The webs can be secured by an adhesive, applied to portions of the first and/or second web, or by ultrasonic bonding, to thereby fabricate the composite web. In another embodiment, a vacuum roll receives and forms at least one groove in the first web and advances the first web to a nip roll that secures a reference surface of the first web to the second web in a nip formed by the vacuum roll and the nip roll while maintaining the groove in the first web. The webs are then advanced to an urging apparatus including a mating roll that mates with the vacuum roll to stretch and urge a facing portion of the second web inwardly into the groove and into securement with the first web thereby to fabricate the composite web.

46 Claims, 7 Drawing Sheets

METHOD AND APPARATUS FOR PRODUCING A COMPOSITE WEB HAVING TRANSVERSE STRETCH

FIELD OF THE INVENTION

The present invention relates to methods and apparatus for producing a web having transverse stretch. The method includes placing a layer of discontinuous or continuous elastomeric material on a layer of material. The final product comprises a web having transverse stretch. The web can be used for fabricating absorbent articles or other products.

BACKGROUND OF THE INVENTION

Conventional webs having stretch in the machine direction are known in the art. Other webs have been manufactured to have stretch in the transverse direction.

For example, U.S. Pat. No. 5,451,219 to Suzuki et al discloses a composite sheet formed by an elastic web secured to a non-woven fabric. The non-woven fabric is tucked into a mold as shown in Suzuki et al at FIGS. 22 and 23.

U.S. Pat. Nos. 4,240,866 and 4,285,747 to Rega disclose an apparatus and method for manufacturing a product having elastic elements disposed in the transverse direction. The elastic material and the web material are joined while the web material is formed into a groove and the elastic material is relaxed. Then a bowed roll generally flattens the web material and forms it into a reverse concave configuration, thereby stretching the elastic material in the center portion. This action brings the center portion of the elastic material into contact with the web material and may adhere the center portion to the web material.

U.S. Pat. No. 4,397,704 to Frick discloses a method and apparatus for applying discrete lengths of elastic strip material to a continuously moving web. The web is placed on a drum having transverse grooves. Strips of elastic material are mounted to the web, on the drum, the strips being oriented in the machine direction of the drum. Therefore, stretch of the absorbent article so created, and as imparted by the elastic strips, is in the machine direction. There is no disclosure, teaching or suggestion in Frick to arrange the grooves or elastic strips for imparting stretch in the transverse direction.

U.S. Pat. No. 4,379,016 to Stemmler et al discloses a method and device for spraying a liquid hot melt material, which hardens to a rubber elastic consistency, onto pleated portions of a web of material. As in Frick, Stemmler et al orient the length of the elastic strip in the machine direction.

SUMMARY OF THE DISCLOSURE

The present invention relates to methods and apparatus for fabricating composite webs, and focuses on forming composite webs having transverse stretch. The methods include, in a first web of material having a reference surface, forming at least one groove in the first web, displaced from the reference surface, securing a second web of stretchable material to the first web at first and second adjacent portions of the first web on opposing sides of the groove while maintaining the groove in the first web, such that, at the groove, a facing portion of the second web is in facing relationship with and spaced from, the first web, urging the facing portion of the second web into the groove of the first web and thereby stretching the second web, and securing the second web to the first web in the groove while the facing portion of the second web is in the stretched condition.

In most embodiments, the facing portion of the second web is urged into surface-to-surface relationship with the first web in the first groove thereby securing the webs to each other in surface-to-surface relationship over substantially the entirety of the facing portion of the second web.

Another embodiment includes forming at least two grooves in the first web, each groove being displaced from the reference surface. A transverse cross-section of the web, across the at least two grooves, can conform to a sinusoidal wave pattern.

In another embodiment, adhesive is applied to at least one of the first and the second webs. A print roll can be utilized to apply the adhesive to the reference surface at first and second adjacent portions of the first web on opposing sides of the groove such that the first and second webs are secured adhesively to each other. The adhesive can comprise a hot melt adhesive applied to at least one of the first and second webs by a spray nozzle.

In yet another embodiment, ultrasonic energy can be used to secure the first and second webs to each other. Apparatus for securement using ultrasonic energy can comprise an applicator roll securing the second web to the first web in cooperation with respective first and second pressing rolls. The first and second pressing rolls can comprise first and second ultrasonic horns. The applicator roll can comprise an anvil roll. The ultrasonic horns and cooperating anvil, in combination, secure the second web of stretchable material to the first web.

In still another embodiment, the second web has a substantially continuous length corresponding substantially to a continuous length of the first web.

In a further embodiment, the second web comprises discrete lengths of stretchable material secured to a substantially continuous length of the first web at spaced locations on the first web. Activation of the push roll is registered in time and space to thereby force the discrete lengths of stretchable material into the groove in the first web.

Typical embodiments include reducing the edge-to-edge transverse width of the first web while forming at least one groove, and maintaining the reduced width of the first web while urging the respective facing portion of the second web into the groove of the first web.

In still a further embodiment, the step of forming the at least one groove includes advancing the first web along a forming plow, and thereby forming the groove while passing the first and second adjacent portions of the first web across first and second opposing pressing rolls on opposing sides of the groove, thereby retaining the adjacent first and second portions of the first web at or propinquant the reference surface. The step of securing the second web to the first web can include using an applicator roll to transport the second web and thereby to place the second web in contact with the first web in a relaxed condition. The applicator roll, in combination with the first and second pressing rolls, secure the second web to the first web at the first and second adjacent portions of the first web. The groove formed by the plow can have a depth of from about 2 centimeters to about 10 centimeters.

In yet another embodiment, the urging apparatus comprises a push roll. The push roll, in cooperation with third and fourth pressing rolls, intermittently forces the facing portion of the stretchable material into the groove and into physical contact with the web while using third and fourth pressing rolls to stabilize the positioning of the first and second adjacent portions of the web. The push roll can comprise an ultrasonic anvil having two opposing surfaces oriented at an angle of between about 45 degrees and about 60 degrees with respect to a plane defined by the stretchable material before the stretchable material is acted upon by the push roll. Opposing surfaces of the push roll cooperate with respective ultrasonic horns, preferably rotary ultrasonic horns, to thereby secure at least part of the facing portion of the stretchable material to the web. The push roll can have a lobed cross-section to provide timed intermittent bonding.

In yet another embodiment, the groove forming apparatus comprises a vacuum roll having at least one ridge, and a valley, extending about the circumference of the vacuum roll. Vacuum ports are located in the valley of the vacuum roll. The groove in the web is formed by applying vacuum at the vacuum ports. The ridge can, in some embodiments, extend intermittently about the circumference of the vacuum roll.

In yet another embodiment, the securing apparatus comprises a nip roll, the nip roll in combination with the vacuum roll forming a nip. The combination of the nip roll and the vacuum roll secures the second web to the first web. A facing portion of the second web remains displaced from the first web. The nip roll applies pressure to the vacuum roll at at least one ridge of the vacuum roll.

In a further embodiment, the urging apparatus comprises a mating roll having a ridge, cooperating with the valley on the vacuum roll. The ridge on the mating roll urges the second web into the groove in the first web to thereby effect securing the first and second webs in surface-to-surface contacting relationship with each other. Operation of the mating roll can adhesively secure the stretchable material and the web across substantially the entirety of the surface-to-surface relationship of the respective contacting surfaces.

In typical embodiments, the forming of at least one groove includes forming the groove along a length of the first web.

In some embodiments, an apparatus for fabricating a composite web includes groove forming apparatus forming at least one groove in the web, securing apparatus securing the stretchable material to the web while the web is in the grooved configuration such that, at the groove, a facing portion of the stretchable material is spaced from the continuously conveyed web and is in facing relationship with the continuously conveyed web, and urging apparatus urging the facing portion of the stretchable material into the groove of the continuously conveyed web and thereby stretching the stretchable material, and securing the stretchable material to the continuously conveyed web in the groove while the facing portion of the stretchable material is in the stretched condition.

In some embodiments, a knife roll cuts the stretchable material into discrete lengths before the stretchable material is secured to the web by the applicator roll.

In yet another embodiment, the apparatus for fabricating a composite web having a length and transverse stretch comprises groove forming apparatus forming a groove in a first web of material having a reference surface, the groove being displaced from the reference surface, securing apparatus securing a second web of stretchable material to the first web at first and second adjacent portions of the first web on opposing sides of the groove while maintaining the groove in the first web such that, at the groove, a facing portion of the second web is spaced from the first web and is in facing relationship with the first web, and urging apparatus urging the facing portion of the second web into the groove and thereby stretching the second web, and securing the second web to the first web in the groove while the facing portion of the second web is in the stretched condition. The securing apparatus generally secures the second web to the first web on opposing sides of the groove while the second web is in a relaxed, substantially unstretched condition.

The invention is not limited in its application to the details of the construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components. Further, the above drawings are not drawn to scale and do not so limit the invention.

DETAILED DESCRIPTION OF THE ILLUSTRATED EMBODIMENTS

The present invention is directed toward apparatus and methods for fabricating a web having transverse stretch. An exemplary method secures a stretchable material to a web of material to provide transverse stretchability for the web.

Figure 1:
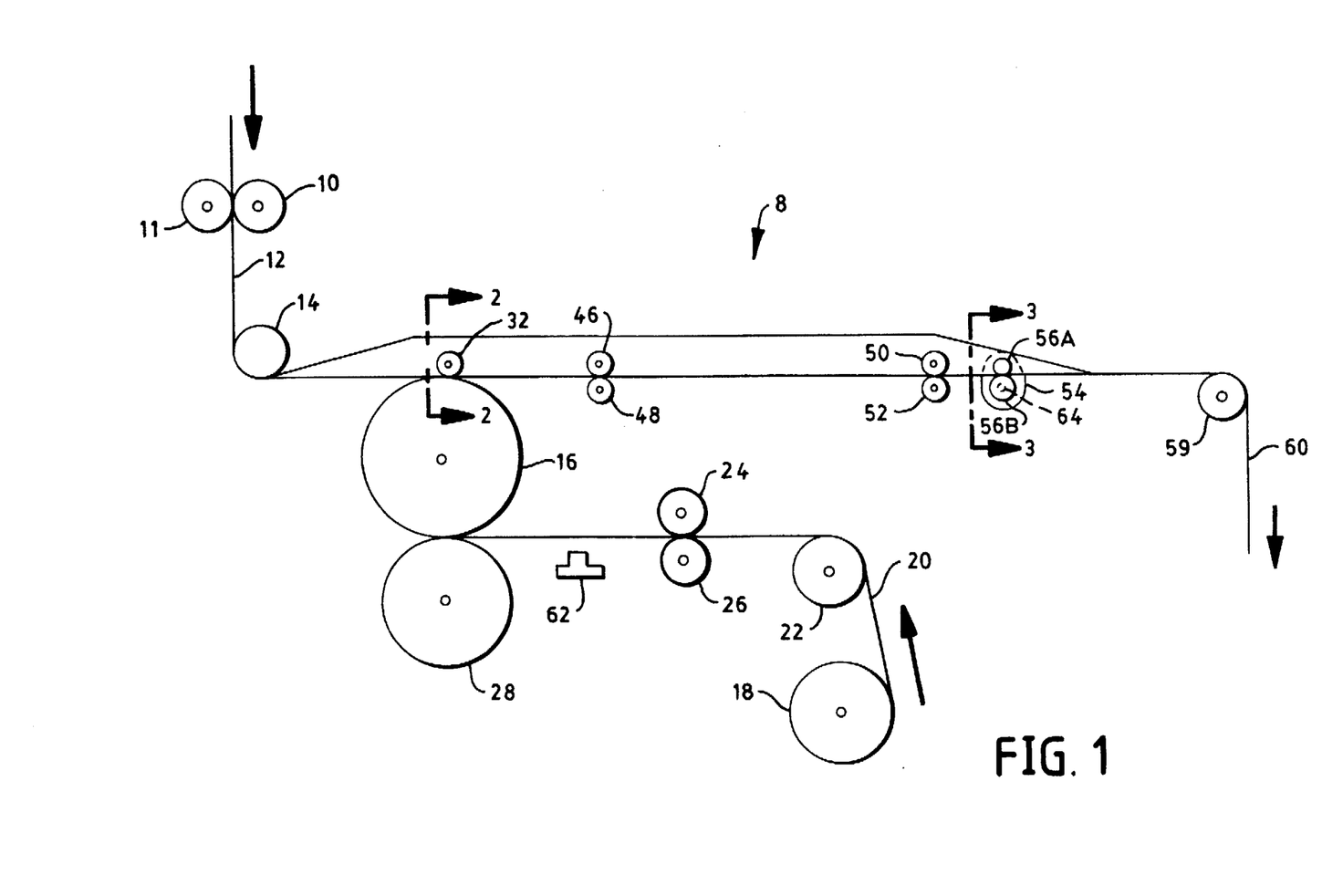
FIG. 1 shows a side elevation of a layout of apparatus of the invention, for fabricating a web.

FIG. 1 shows apparatus 8 for fabricating a web. Nip draw rolls 10, 11, draw a web 12 comprising a first layer of material from a supply roll (not shown) toward turning roll 14. Turning roll 14 turns web 12 toward applicator roll 16. Meanwhile, second nip draw rolls 24, 26 draw second web 20 of stretchable material from supply roll 18, around turning roll 22, and direct second web 20 toward applicator roll 16. In some embodiments, knife cutting roll 28, in cooperation with applicator roll 16, cuts second web 20 of stretchable material into discrete lengths thereof.

Applicator roll 16 can be described as a securing apparatus which applies second web 20 to first web 12. However, before such application occurs, groove forming apparatus, comprising a forming plow 30, shown in FIG. 2, alters the shape of first web 12. Forming plow 30, in combination with pressing rolls 32, 34 shown in FIG. 2 form groove 36 along the length of first web 12 substantially between press rolls 32, 34 and press rolls 56A, 56B. In the embodiment shown in FIG. 2, reference surface 40 is illustrated by two surface elements 42, 44. Surface elements 42, 44 are comprised in first and second adjacent portions of first web 12, adjacent groove 36, and on opposing sides of groove 36. Pressing rolls 46, 48, 50, 52 shown in FIG. 1 assist in guiding the web and in maintaining groove 36 in first layer 12 along the full length thereof between opposing rolls 32 and push roll 54. Urging apparatus includes a push roll 54 and pressing rolls 56A, 56B, 58A, 58B. Push roll 54 urges second web 20 inward into contact with, and into securement with, first web 12. Turning roll 59 then turns the composite web 60 toward a subsequent station (not shown). In some embodiments, adhesive applicator 62 can apply adhesive to second web 20.

One of rolls 10, 11 is driven and thus draws first web 12 from a supply roll (not shown). While rolls 10, 11 are shown positioned upstream of turning roll 14, the location of draw rolls 10, 11 is generally not critical to the invention. Other draw rolls (not shown) downstream in the process from turning roll 59 can draw first web 12, and, in combination, completed web 60, through apparatus 8.

Figure 2:
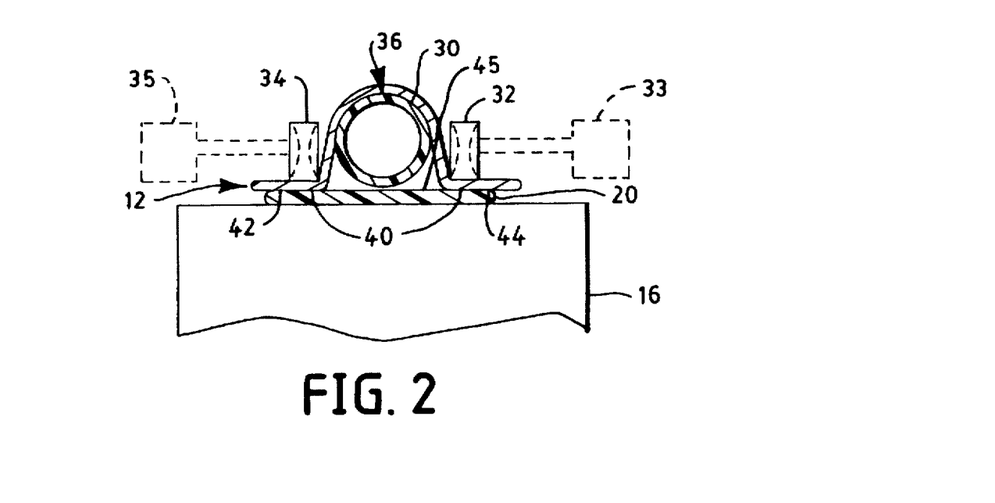
FIG. 2 shows a cross-sectional view of groove forming apparatus and securing apparatus taken at 2—2 in FIG. 1.

Turning roll 14 turns first web 12 toward applicator roll 16 and forming plow 30 as shown in FIG. 2.

First web 12 can be formed from a single layer, or from multiple components, layers, or partial layers, of material. In some embodiments, the resulting web can be substantially impermeable to liquids. First web 12 can be stretchable in the machine direction. In some embodiments first web 12 is preferably non-stretchable. Non-stretchable defines a maximum elongation of less than 5%. A typical first web 12 may be a thin plastic film or other flexible liquid-impermeable material. For example, first web 12 can be formed from a polyethylene film having a thickness of from about 0.012 millimeter to about 0.051 millimeter. When it is desirable that first web 12 have a more clothlike feeling, it may comprise a polyethylene film laminated to a surface of a nonwoven web, such as a spunbonded web of polyolefin fibers. For example, a polyethylene film having a thickness of about 0.015 millimeter may have thermally or otherwise laminated thereto a spunbonded web of polyolefin fibers having a thickness from 1.5 to 2.5 denier per filament, which nonwoven web has a basis weight of about 24 grams per square meter. Further, first web 12 can be formed of a woven or nonwoven fibrous web which has been totally or partially constructed or treated to impart a desired level of liquid impermeability to selected regions. Still further, first web 12 may optionally be composed of a microporous material which permits vapors to escape therethrough while preventing liquid from passing through the first web.

One of draw rolls 24, 26 is driven and thus draws second web 20 from supply roll 18. While draw rolls 24, 26 are shown positioned downstream of turning roll 22, the location of draw rolls 24, 26 generally is not critical to the invention. Other draw rolls downstream from apparatus 8 can draw second web 20 through the apparatus.

Second web 20 comprises a material stretchable at least across the transverse dimension of first web 12, and optionally stretchable along the length of first web 12. As used here, direction of stretch of web 20 is taken with respect to the length of web 12. As used here, "stretchable" defines an elongation of at least 5%. Materials used to make second web 20 can comprise, for example, a laminate including first and second outer nonwoven facing layers on opposing sides of an elastomeric core layer, the elastomeric core layer comprising a thermoplastic elastomeric composition such as a styrene ethylene butylene styrene terpolymer. Second web 20 can also comprise a plurality of elastomeric elements comprising strands, ribbons or the like secured in a stretched condition to a nonelastomeric substrate, the elastomeric elements being so oriented as to extend across the width of first web 12 in the composite web, thus to provide stretchability to the composite web in the transverse direction.

Examples of other materials of which all or part of second web 20 may be comprised include, without limitation, spandex/nonwoven laminated webs, elastomeric meltblown webs, cross-machine direction stretchable web materials made with stretchable nonwovens, stretchable foam webs and the like. Second web 20 can be made from rubber, either natural or synthetic, or other well known elastic, thermoplastic film materials.

In some embodiments, optional knife cutting roll 28 cuts discrete, preferably transverse, lengths of second web 20. Applicator roll 16 provides an anvil for knife cutting roll 28 when cutting second web 20. Applicator roll 16 secures the discrete lengths of second web 20 to first web 12 by operating intermittently, or at a variable speed, to thereby apply the discrete lengths at spaced locations along the length of the first web.

Figure 4:
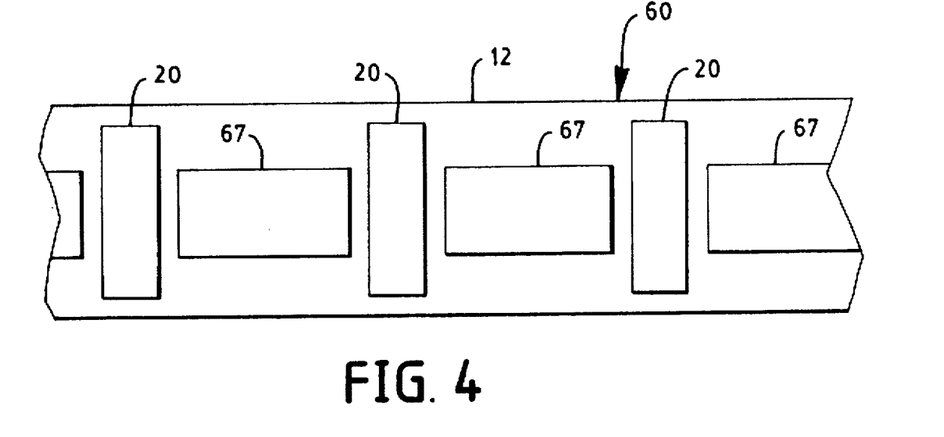
FIG. 4 shows an exemplary first web having discrete second layers mounted thereon.

Applicator roll 16, in cooperation with pressing rolls 32, 34, thus secures transversely oriented discrete lengths of second web 20 to a substantially continuous length of first web 12 at transversely and longitudinally spaced locations as shown in FIG. 4. A full description of an exemplary applicator roll is set forth in U.S. patent application Ser. No. 08/381,364 titled "Method and Apparatus for Placing Discrete Parts onto a Moving Web" by Rajala et al, filed Jan. 31, 1995, and hereby incorporated by reference in its entirety.

In other embodiments where second web 20 comprises a substantially continuous length of stretchable material and knife cutting roll 28 is generally not operated, Applicator roll 16 can comprise a nip roll, which need not be a vacuum roll, and can operate at a constant speed, rather than a variable speed, to continuously transfer and secure substantially continuous second web 20 to substantially continuous first web 12.

FIG. 2 more clearly illustrates a securing apparatus for securement of second web 20 to first web 12. Forming plow 30 preferably has a tubular shape and preferably is oriented at upward and downward angles to the general direction of movement of web 12, toward the respective front and rear ends of the plow. Thus forming plow 30 forms groove 36 in first web 12 along the length of the forming plow. Forming plow 30, for example, can be made from a smooth plastic or metal material. As groove 36 is formed in first web 12, the edge-to-edge transverse width of the first web is reduced. Forming plow 30 maintains the reduced width of the first web along substantially the entire length of apparatus 8. Single groove 36 can have a depth of from about 2 centimeters to about 10 centimeters with respect to reference surface 40.

Pressing rolls 32, 34 and applicator roll 16 cooperate with forming plow 30 to form groove 36. First and second surface elements 42, 44 of first web 12 between applicator roll 16 and pressing rolls 32, 34 form reference surface 40. Second web 20 is secured to respective first and second surface elements 42, 44 at reference surface 40. First and second surface elements 42, 44 are retained at or propinquant reference surface 40 at least during securement of the respective webs. First and second surface elements 42, 44 of first web 12 are secured to second web 20 while the first web is in the grooved configuration such that, at groove 36, a facing portion 45 of the second web is spaced from the first web and is in facing relationship with the first web. Securement preferably occurs while second web 20 is in a substantially relaxed, unstretched condition.

In some embodiments, pressing rolls 32, 34, cooperating with applicator roll 16, secure first web 12 and second web 20 to each other through operation of adhesive applied between the respective webs. Pressing rolls 32, 34 can have widths greater than the widths shown in FIG. 2, and the width of second web 20 can be correspondingly wide, such that the entire widths of first and second surface elements 42, 44 of first web 12 are secured to second web 20. Second web 20 preferably has substantially the same width as first web 12 after at least one groove 36 is formed in the first web. See FIGS. 3 and 3A.

In other embodiments, however, where adhesive is not utilized, pressing rolls 32, 34 comprise respective ultrasonic horns connected to respective waveguides 33, 35. In these embodiments, vacuum applicator roll 16 acts as the anvil cooperating with the respective ultrasonic horns. Ultrasonic energy transferred to first web 12 and second web 20 from ultrasonic horns 32, 34, secures the respective webs to each other. Exemplary disposition of ultrasonic waveguides is illustrated in dashed outlines in FIG. 2.

Pressing rolls 46, 48, 50, 52 and optionally other pressing rolls (not shown) maintain groove 36 in first web 12 along the length of forming plow 30. While two sets of pressing rolls are shown, any number including more or fewer pressing rolls sufficient to maintain groove 36 in first web 12, are suitable for purposes of the invention.

Figure 3:
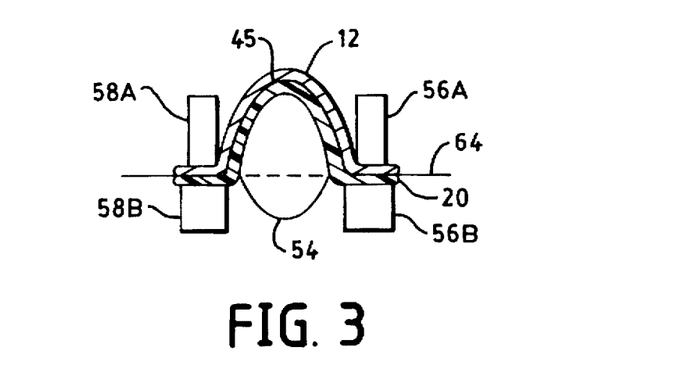
FIG. 3 shows a cross-section of an urging apparatus taken at 3—3 in FIG. 1.

As illustrated in FIG. 3, push roll 54 pushes facing portion 45 of second web 20 inwardly into groove 36 of the continuously conveyed first web 12 and thereby transversely stretches the second web. Adhesive previously applied to one or both of first web 12 and second web 20 then adheres the respective first and second webs to each other while the second web is in a stretched condition. The amount of transverse stretch in second web 20 when mounted to first web 12 can vary from about 10% to about 50% percent elongation, and more preferably from about 20% to about 25% elongation when second web 20 is urged into the groove of first web 12. The transverse potential stretch of final composite web 60 is substantially the same as the transverse stretch of second web 20 when urged into the groove of first web 12.

In the embodiment shown in FIGS. 1–3, push roll 54 has an axis 64 and an exemplary shape. Thus every revolution of push roll 54 about axis 64 pushes facing portion 45 of second web 20 inwardly and into surface-to-surface contact with first web 12. Push roll 54, having an axis 64, preferably is utilized in embodiments of the invention where second web 20 comprises discrete elements applied to first web 12. Push roll 54 is timed or registered with second web 20 to intermittently rotate about axis 64 such that the surface of roll 54 remote from axis 64 forces the discrete lengths of stretchable material into groove 36 in first web 12 when the respective discrete lengths are properly positioned along the length of web 12. The discrete lengths are thereby stretched when pushed into groove 36, and are bonded to first web 12 when so pushed into contact with web 12.

Rather than intermittent rotation, push roll 54 can rotate with a continuous but variable speed, similarly timed to force the discrete lengths of stretchable web 20 into groove 36.

Pressing rolls 56A, 56B and pressing rolls 58A, 58B on opposing sides of and adjacent push roll 54 guide web 12 through the reduction in depth of the groove beyond direct contact with forming plow 30. Thus pressing rolls 56A, 56B, 58A, 58B stabilize the positioning of first and second adjacent portions of first web 12. When push roll 54 urges the second web toward the first web, lower pressing rolls 56B, 58B assist in maintaining the earlier securement of second web 20 to first web 12 at reference surface 40. Reduction in width of first web 12, which coincides with formation of groove 36, is also maintained by pressing rolls 56A, 56B, 58A, 58B.

In embodiments of the invention where second web 20 comprises a substantially continuous web of material, push roll 54 can have a cylindrical shape with a central axis (not shown) such that the push roll substantially continuously urges second web 20 inward into surface-to-surface relationship with first web 12. The sides of push roll 54 can be tapered or otherwise shaped to provide substantially even force to second web 20 at facing portion 45 being secured to first web 12.

While adhesive applicator 62 is shown applying adhesive to second web 20 in FIG. 1, other arrangements are contemplated. For example, adhesive applicator 62 can apply adhesive to first web 12 instead of second web 20 at a location prior to securement of the webs to each other, such as while second web 20 is being transported by knife cutter roll 28.

Adhesive applicator 62 can comprise a print roll applying adhesive to reference surface 40 at first and second adjacent portions 42, 44 of first web 12 on opposing sides of groove 36.

As a second exemplary illustration, adhesive applicator 62 can comprise a single spray nozzle, or multiple spray nozzles, applying adhesive, such as hot melt adhesive, to first web 12 or second web 20, or both. The adhesive preferably has a high level of tackiness.

Figure 3A:
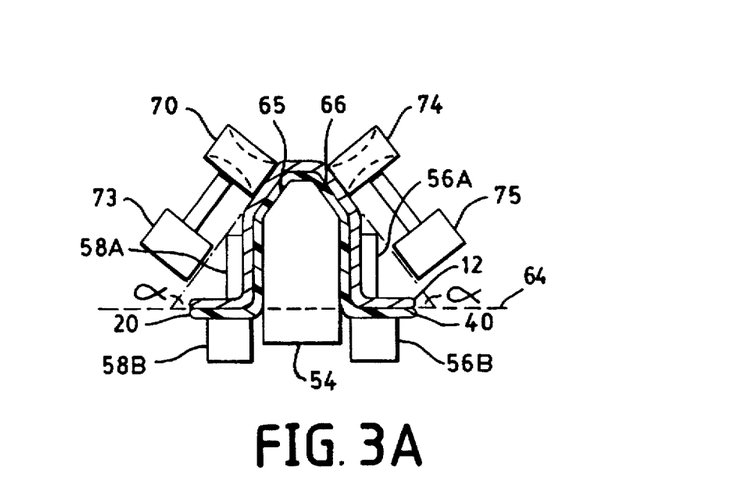
FIG. 3A shows a modification of the urging apparatus shown in FIG. 3.

FIG. 3A illustrates an alternative embodiment of push roll 54. In this embodiment, push roll 54 comprises an ultrasonic anvil having an axis 64 and surfaces 65, 66. Ultrasonic energy is supplied to ultrasonic horn 70 through waveguide 73. Ultrasonic energy is supplied to ultrasonic horn 74 through waveguide 75. Horns 70 and 74 act upon respective surfaces 65, 66 to ultrasonically bond first web 12 to second web 20. Surfaces 65, 66 preferably are flat in cross-section as shown in FIG. 3A, to enhance ultrasonic bonding. Surfaces 65, 66 of push roll 54 are oriented at angles "α" of from about 45 to about 60 degrees with respect to the plane of reference surface 40. Pressing rolls 56A, 56B, 58A, 58B operate as described earlier. The respective pressing rolls assist in maintaining groove 36 in first web 12 when push roll 54 intermittently presses facing portion 45 of second web 20 inwardly into surface-to-surface contact with first web 12.

FIG. 4 shows an exemplary composite web 60 formed by apparatus 8 of FIG. 1 from webs 12 and 20. First web 12 can comprise the outer cover and second web 20 can comprise elastomeric waistbands for use as part of an absorbent article or other product. FIG. 4 also illustrates an absorbent material or absorbent core 67 secured to first web 12 in an earlier or later step than the securing of second web 20 to first web 12 described earlier herein.

While fabricating an outer cover having elastomeric waistbands is one potential use of the invention, others are contemplated. For instance, in some embodiments first web 12 can comprise a bodyside liner for an absorbent article.

As contemplated herein, web 60 generally comprises an intermediate product from which individual absorbent articles are severed. Other potential uses of composite web 60 can be unrelated to absorbent articles.

Figure 5:
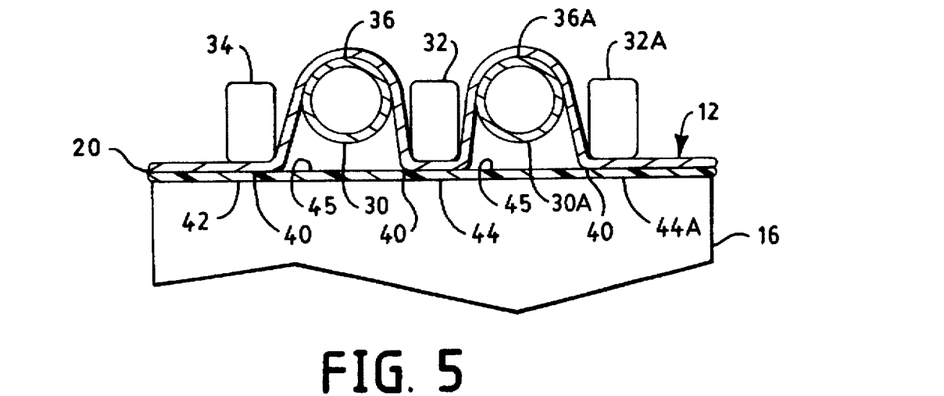
FIG. 5 shows a cross-section as in FIG. 2, forming multiple grooves in the web.

FIG. 5 shows another embodiment of the invention of FIGS. 1–3. In this embodiment, the forming plow comprises two forming plows 30, 30A generally mounted substantially parallel to each other. Three pressing rolls 34, 32, 32A are arranged so each forming plow is between a pair of the respective pressing rolls. Reference surface 40 includes surface elements 42, 44, 44A of first web 12. Applicator roll 16 cooperates with the respective pressing rolls 34, 32, 32A to secure first web 12 and second web 20 at the reference surface except for grooves 36, 36A formed by forming plows 30, 30A. Thus two facing portions 45 of web 20 are spaced from web 12. In the embodiment of FIG. 5, push roll 54 includes a corresponding second push roll element (not shown) to force second web 20 into second groove 30A. This embodiment operates like the embodiments described earlier for both discrete and continuous lengths of second web 20 except for the addition of another groove 30A. While two grooves are shown in FIG. 5, any suitable number of additional grooves are contemplated.

Figure 6:
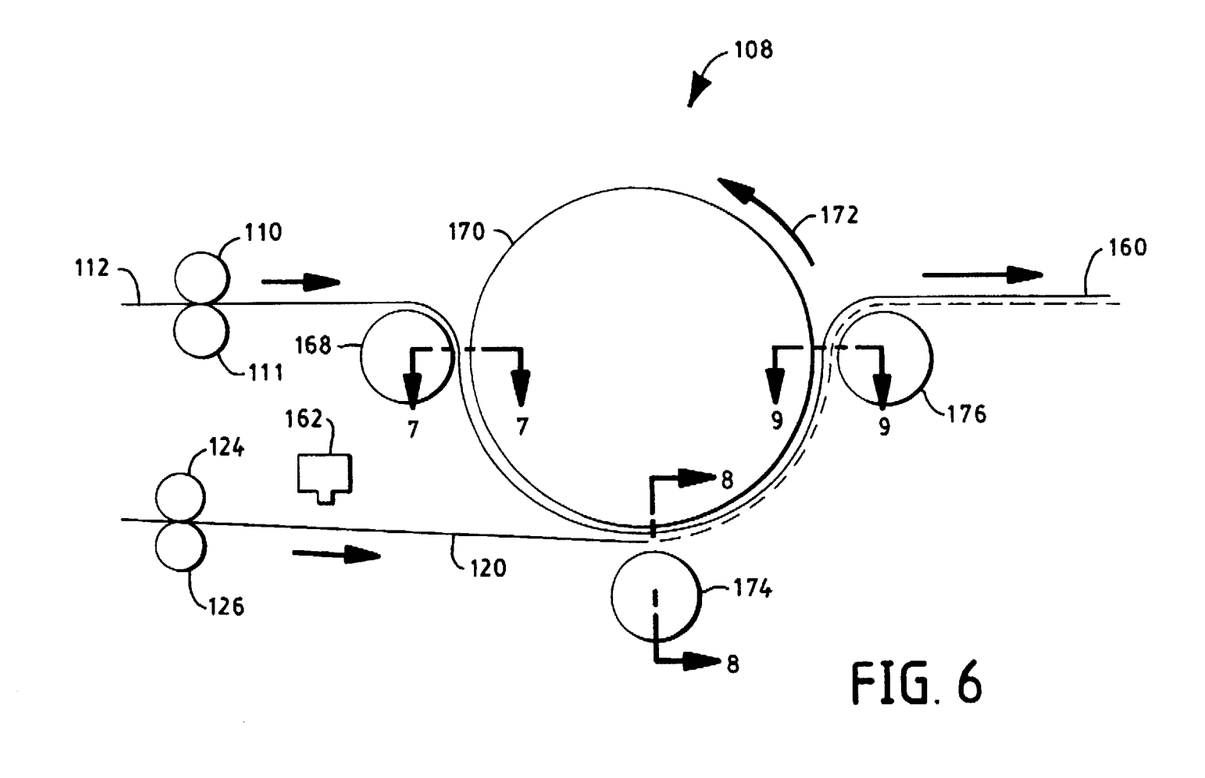
FIG. 6 shows a second embodiment of a side elevation of a layout of apparatus of the invention.

FIG. 6 shows a second embodiment of apparatus 108 of the invention wherein the prefix "1" indicates the second embodiment. Second and third digits are used in common with the first embodiment to represent structure corresponding to like structure in the first embodiment. Apparatus 108 includes first and second draw rolls 110, 111 drawing first web 112 from a supply roll (not shown) or other location, such as a different work station. Turning roll 168 turns first web 112 and transfers the first web to vacuum roll 170. Vacuum roll 170 rotates in the direction shown by arrow 172 and advances first web 112 to nip roll 174. Draw rolls 124, 126 draw second web 120 from a supply roll (not shown) toward nip roll 174. Adhesive applicator 162 applies adhesive to second web 120 before the second web reaches nip roll 174. Nip roll 174 and vacuum roll 170 form a nip. The pressure at the nip between the nip roll 174 and vacuum roll 170, in combination with adhesive applied earlier, secures at least part of second web 120 to first web 112. Mating roll 176, in combination with vacuum roll 170, urges facing portion 145 of second web 120 inwardly into groove 136 of first web 112 and into contact with the first web while the second web is in a stretched condition. Thus composite web 160 is formed from first and second webs 112, 120.

Figure 7:
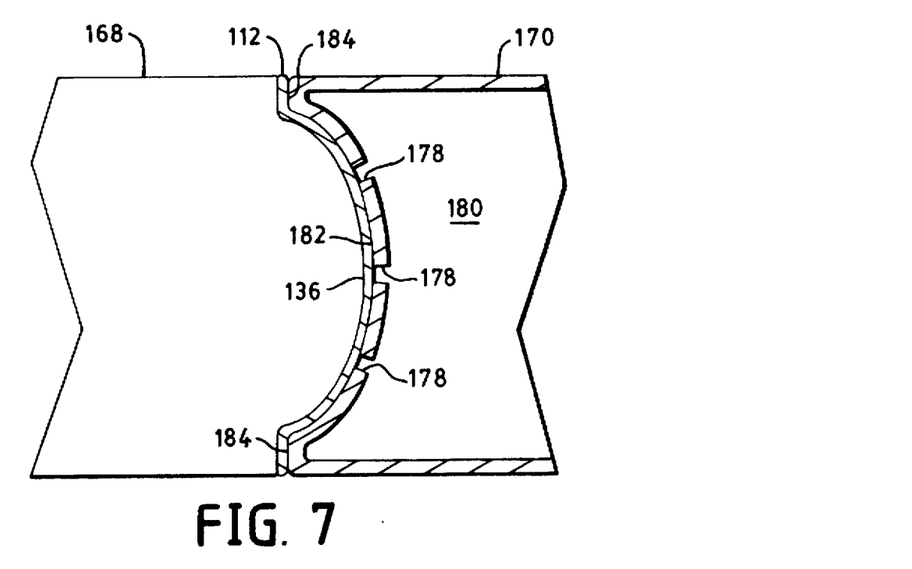
FIG. 7 shows a cross-sectional view of a nip formed by a vacuum roll and a turning roll, and is taken at 7—7 in FIG. 6.

As shown in FIG. 7, turning roll 168 transfers first web 112 to vacuum roll 170. Vacuum ports 178 in vacuum roll 170 lead to vacuum chamber 180 which is connected to a vacuum device (not shown). Thus ports 178 seat and retain first web 112 on vacuum roll 170. While only three ports 178 of the multiple ports of vacuum roll 170 are shown in FIG. 7, any appropriate number of ports in any appropriate pattern can be utilized about the circumference of the vacuum roll to secure and retain the first web to the vacuum roll. One example of a vacuum roll suitable for use with this embodiment is set forth in U.S. patent application Ser. No. 08/381, 364 titled "Method and Apparatus for Placing Discrete Parts onto a Moving Web" by Rajala et al, earlier incorporated by reference.

While FIG. 7 shows turning roll 168 both turning and seating first web 112 on vacuum roll 170, turning roll 168 need not substantially match or mate with the surface of vacuum roll 170. The operation of turning roll 168 is acceptable so long as the turning roll properly places first web 112 on vacuum roll 170 for vacuum securement thereto. Thus a mating arrangement is not required.

Turning again to FIG. 7, both valley 182 and ridges 184 of vacuum roll 170 preferably extend about the circumference of the vacuum roll to form groove 136 in first web 112. In some embodiments, ridges 184 can extend intermittently about the circumference of vacuum roll 70.

Figure 8:
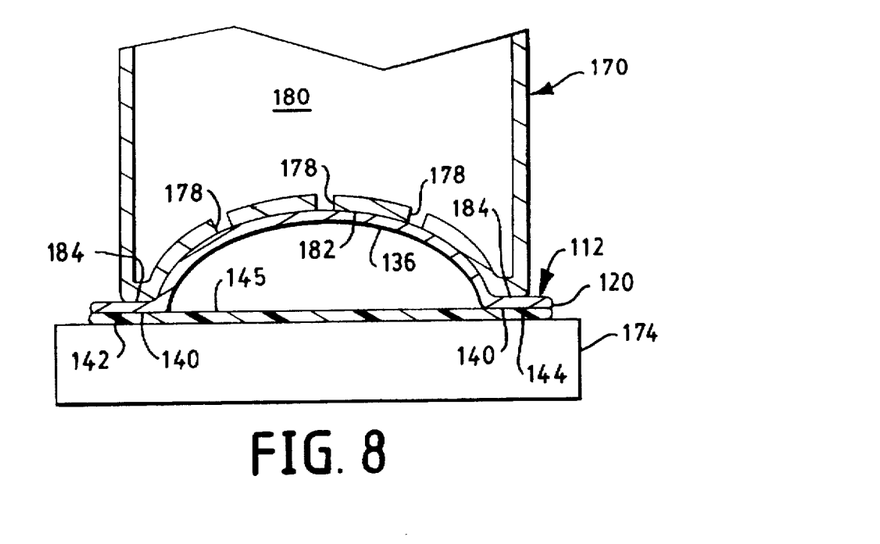
FIG. 8 shows a cross-sectional view of a nip formed by the vacuum roll and a nip roll, and is taken at 8—8 in FIG. 6.

Once placed on vacuum roll 170, first web 112 advances in direction 172, and reaches nip roll 174 as shown in FIGS. 6 and 8. Surface elements 142, 144 of reference surface 140 comprise first and second adjacent portions of first web 112 on opposing sides of groove 136. Adhesive applicator 162 applies adhesive to second web 120 before the second web reaches nip roll 174. At least surface elements 142, 144 of first web 112 are secured to second web 120 due to the presence of the adhesive and pressure between ridges 184 of nip roll 174 and vacuum roll 170. The surface elements 142, 144 of first web 112 are secured in surface-to-surface relationship to second web 120. Meanwhile facing portion 145, in the center of second web 120, remains spaced from the first web and in facing relationship with the first web.

Figure 9:
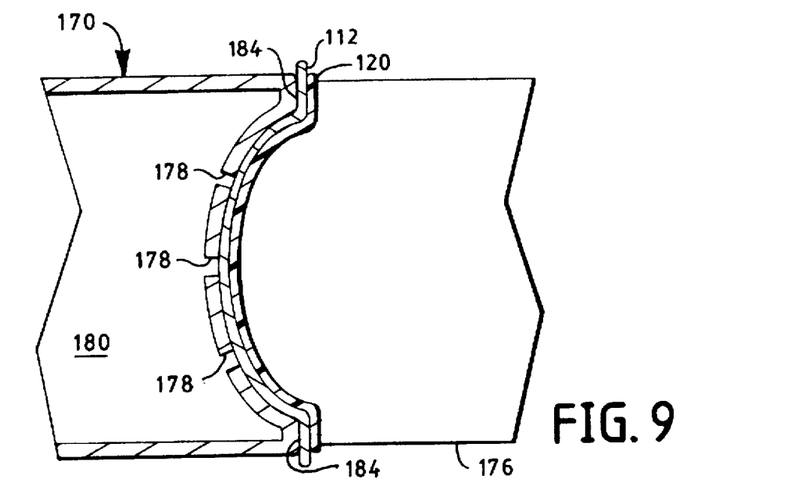
FIG. 9 shows a cross-sectional view of the vacuum roll and a mating roll taken at 9—9 in FIG. 6.

First web 112 and second web 120 then advance by rotation of vacuum roll 170 to mating roll 176 as shown in FIG. 9. Mating roll 176, cooperating with vacuum roll 170, comprises an urging apparatus urging facing portion 145 of second web 120 inwardly into groove 136 of first web 112, and thereby stretching web 120 along the transverse dimension of web 112. Stretching second web 120 in the transverse direction, and applying pressure and/or energy to first web 112 and the second web, secures the first and second webs over substantially their entire contacting surface by e.g. adhesive or ultrasonic bonding. Composite web 160, comprising the webs 112, 120 has a transverse stretch property as it leaves vacuum roll 170.

The embodiment of FIGS. 6–9 can have ultrasonic horns and anvils arranged to secure first and second webs 112, 120 in combination with, or in place of adhesive from adhesive applicator 162.

Figure 7A:
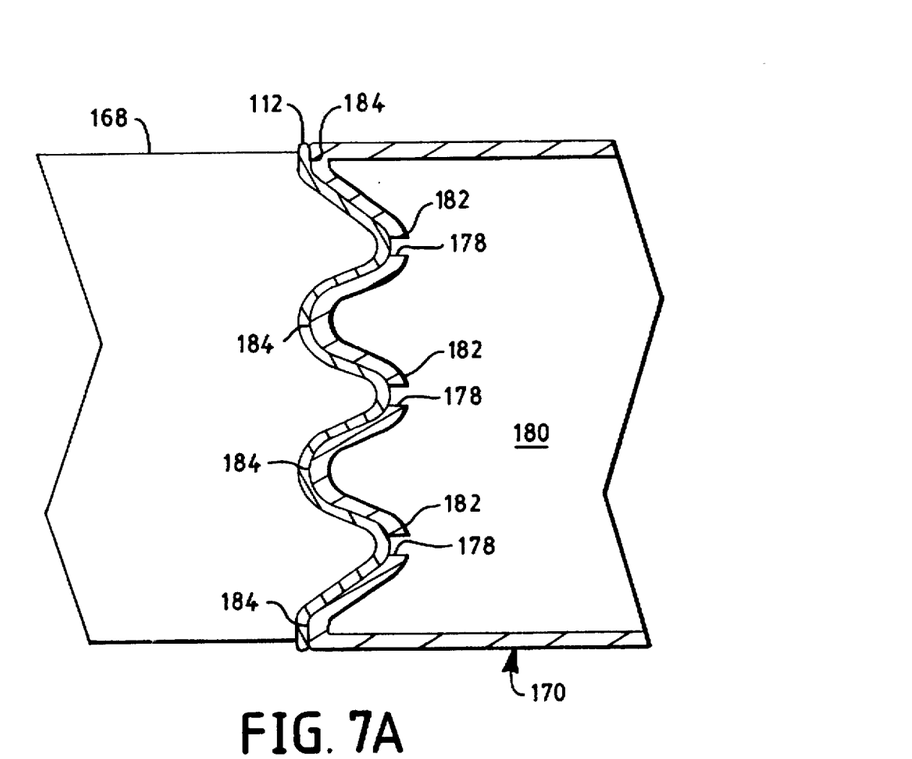
FIG. 7A shows a modification of the nip of FIG. 7, forming multiple grooves in the web.
Figure 8A:
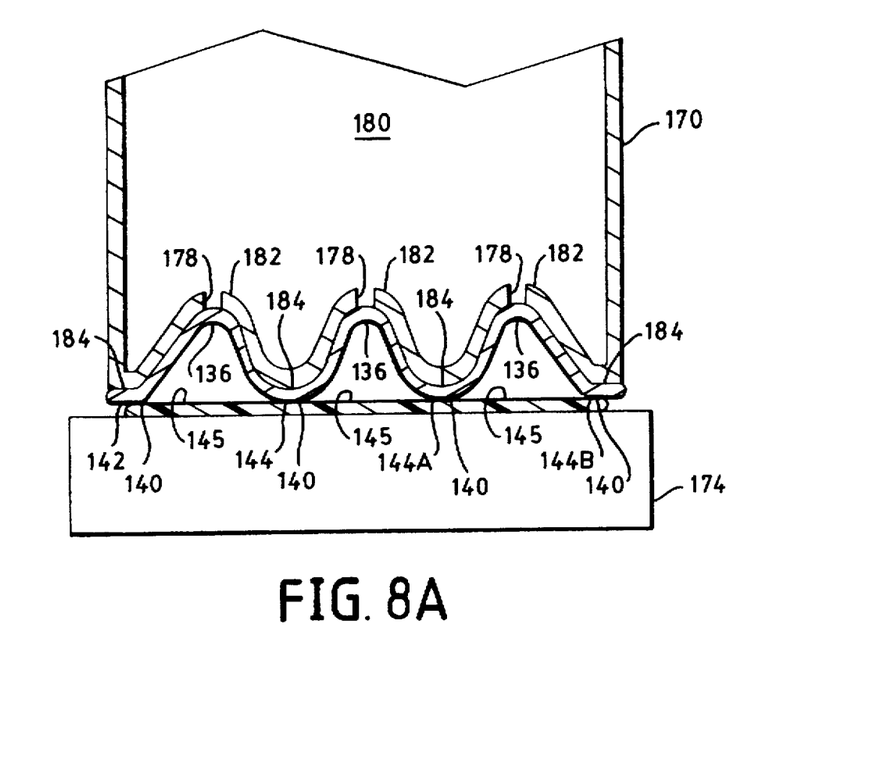
FIG. 8A shows a modification of the nip of FIG. 8, forming multiple grooves in the web.
Figure 9A:
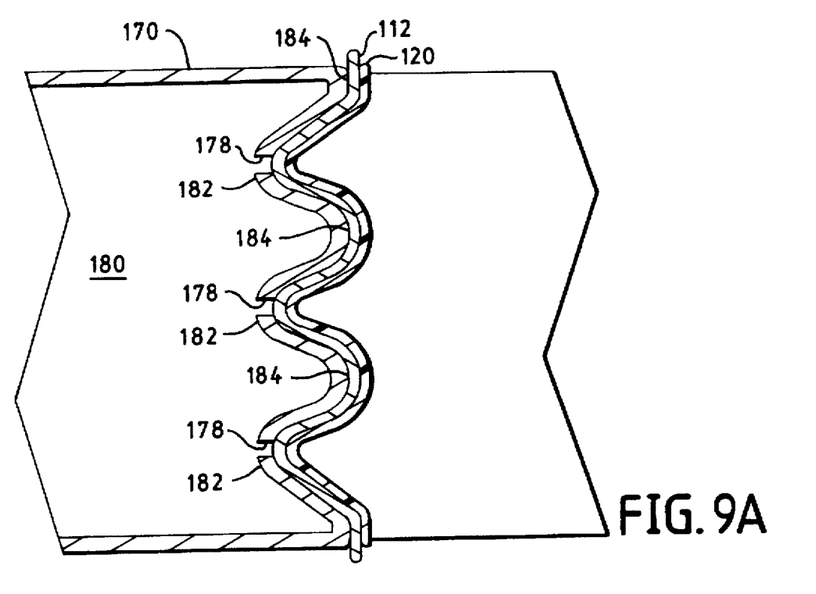
FIG. 9A shows a second embodiment of the view of FIG. 9 having multiple grooves.

FIGS. 7A, 8A and 9A show another variation of the embodiment illustrated in FIG. 6 wherein multiple grooves 136 are formed in web 112. This variation functions according to the illustrations of FIGS. 7, 8 and 9 except for the multiple grooves. As shown in FIG. 7A, vacuum roll 170 has multiple ridges 184 and multiple valleys 182. Each valley 182 contains a suitable array of ports 178 about the circumference of vacuum roll 170. Vacuum temporarily secures first web 112 via ports 178 in each respective valley 182 of vacuum roll 170.

The securing apparatus shown in FIG. 8A functions in a manner similar to the function of the securing apparatus of FIG. 8. However, reference surface 140 of first web 112 includes multiple elements 142, 144, 144A, 144B which are secured to second web 120. The adhesive applicator applies adhesive to second web 120 before the second web reaches nip roll 174. At least surface elements 142, 144, 144A, 144B of first web 112 are secured to second web 120 due to the presence of the adhesive and pressure between nip roll 174 at ridges 184, and vacuum roll 170. Thus surface elements 142, 144 of first web 112 are secured in surface-to-surface relationship to second web 120. Meanwhile, facing portions 145 of second web 120 remain spaced from first web 112 and in facing relationship with the first web as shown in FIG. 8A. Facing portions 145 correspond to plural grooves 136 of vacuum roll 170. Thus, second web 120 is secured to multiple surface elements 142, 144, 144A, 144B between and outwardly from grooves 136. As illustrated, multiple grooves 136 suggest a sinusoidal wave pattern. Other patterns, such as jagged or zigzag patterns, are also contemplated as part of the invention.

The urging apparatus shown in FIG. 9A functions like the urging apparatus of FIG. 9. Mating roll 176 has a shape substantially conforming to ridges 184 and valleys 182 of vacuum roll 170. In this way, second web 120 is transversely stretched and urged into multiple valleys 182 to secure facing portions 145 of second web 120 in surface-to-surface relationship over substantially the entirety of first web 112. Transversely stretched and secured facing portions 145 of second web 120 are located between relaxed unstretched secured areas corresponding to multiple surface elements 142, 144, 144A, 144B when the first and second webs 112, 120 form composite web 160.

Thus, composite web 160, created by the apparatus shown in FIGS. 7A, 8A, and 9A, has alternating underlying structural areas of transverse stretch and relaxed unstretched secured areas, and thus differs from webs formed with only a single groove or valley in its multiplicity of stretched and unstretched sites.

Figure 10:
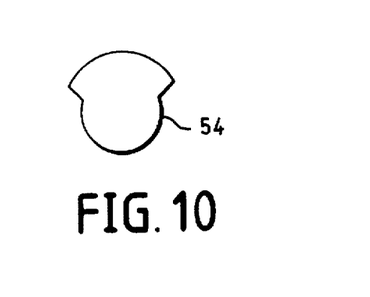
FIG. 10 shows a second embodiment of the push roll having a lobed shape.

In some embodiments, push roll 54 can have an elliptical shape and an eccentric axis. As illustrated in FIG. 10, in other embodiments, push roll 54 can have a lobed shape and a concentric axis.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

Having thus described the invention, what is claimed is:

1. A method of fabricating a composite web having a length and transverse stretch, the method comprising the steps of:
   (a) in a first web of material having a reference surface, forming at least one groove, displaced from the reference surface;
   (b) securing a second web of stretchable material to the first web at first and second adjacent portions of the first web on opposing sides of the groove while maintaining the groove in the first web, such that, at the groove, a facing portion of the second web is in facing relationship with, and spaced from, the first web; and
   (c) urging the facing portion of the second web into the groove of the first web and thereby stretching the second web, and securing the second web to the first web in the groove while the facing portion of the second web is in the stretched condition.

2. A method as in claim 1, the urging in step (c) comprising urging the facing portion of the second web into surface-to-surface relationship with the first web in the groove such that the first and second webs are secured to each other in surface-to-surface relationship over substantially the entirety of the facing portion of the second web.

3. A method as in claim 1, the forming including forming at least two grooves in the first web, each groove being displaced from the reference surface.

4. A method as in claim 1, including forming the groove to a depth of from about 2 centimeters to about 10 centimeters with respect to the reference surface.

5. A method as in claim 1, the securing step including applying adhesive to at least one of the first and the second webs.

6. A method as in claim 5, the step of applying adhesive including using a print roll and thereby applying adhesive to the reference surface at first and second adjacent portions of the first web on opposing sides of the groove.

7. A method as in claim 5, the step of applying adhesive including applying a hot melt adhesive to at least one of the first and second webs with a spray nozzle.

8. A method as in claim 1, the securing including applying ultrasonic energy to secure the first and second webs to each other.

9. A method as in claim 1, including securing a substantially continuous length of the second web to a corresponding substantially continuous length of the first web.

10. A method as in claim 1, including securing discrete lengths of the second web to a substantially continuous length of the first web at spaced locations on the first web.

11. A method as in claim 1, including forming at least two grooves in the first web, a transverse cross-section of the web, across the at least two grooves, conforming to a sinusoidal wave pattern.

12. A method as in claim 1, including reducing edge-to-edge transverse width of the first web while forming the at least one groove, and maintaining the reduced width of the first web while urging the respective facing portion of the second web into the at least one groove of the first web.

13. A method as in claim 1, the step of forming the at least one groove including advancing the first web along a forming plow, and thereby forming the groove while passing the first and second adjacent portions of the first web across first and second opposing pressing rolls and thereby retaining the adjacent first and second portions at or propinquant the reference surface.

14. A method as in claim 13, the step of securing the second web to the first web including using an applicator roll to transport the second web and thereby to place the second web in contact with the first web in a relaxed condition, the applicator roll, in combination with the first and second pressing rolls, securing the second web to the first web at the first and second adjacent portions of the first web.

15. A method as in claim 14, the securing step including using first and second ultrasonic horns as the first and second pressing rolls and using a suitable ultrasonic anvil roll as the applicator roll such that the second web is ultrasonically bonded to the first web at the first and second adjacent portions.

16. A method as in claim 13, the urging of the facing portion of the second web into the groove formed in the first web comprising intermittently urging the facing portion of the web into the groove of the first web and thus into physical contact with the first web while using third and fourth pressing rolls to stabilize the positioning of the first and second adjacent portions of the first web.

17. A method as in claim 16, the intermittent urging of the facing portion of the second web into the groove being effected by a push roll mounted for rotation about an axis.

18. A method as in claim 17, the push roll having two opposing surfaces, the opposing surfaces being oriented at angles of between about 45 and about 60 degrees with respect to the reference surface of the first web when the push roll is urging the facing portion of the second web into the groove.

19. A method as in claim 17, including the further step of, when the second web is urged into the groove, ultrasonically bonding the first and second webs to each other against the push roll, in the groove.

20. A method as in claim 17, the second web comprising discrete lengths of the stretchable material, the method including registering activation of the push roll with the second web to thereby force the discrete lengths of stretchable material into the groove in the first web.

21. A method as in claim 1, the amount of transverse stretch in the second web being from about 20% to about 25% elongation when the facing portion of the second web is urged into the groove of the first web.

22. A method as in claim 1, the step of forming the at least one groove in the first web including positioning the first web on a vacuum roll, the vacuum roll having at least one ridge and a valley extending about the circumference of the vacuum roll, and vacuum ports in the valley of the vacuum roll, forming of the groove in the first web comprising applying vacuum at the vacuum ports in the valley.

23. A method as in claim 22, wherein the at least one ridge extends intermittently about the circumference of the vacuum roll.

24. A method as in claim 22, the step of securing the second web to the first and second adjacent portions of the first web comprising applying a nip roll against the vacuum roll to thereby force the second web into contact with the first web, the nip roll applying pressure to the vacuum roll at the at least one ridge of the vacuum roll.

25. A method as in claim 22, the step of urging the second web into the groove of the first web comprising urging a ridge of a mating roll into a respective valley on the vacuum roll, the ridge on the mating roll forcing the second web into the groove in the first web to thereby secure the first and second webs in surface-to-surface relationship to each other.

26. A method as in claim 1, the forming of the at least one groove including forming the at least one groove along a length of the first web.

27. A method as in claim 1, the step of securing the second stretchable web to the first web including securing the second web to the first web on opposing sides of the groove while the second web is in a relaxed, substantially unstretched condition.

28. Apparatus for applying stretchable material to a substantially continuously conveyed web to render the conveyed web stretchable in the transverse direction, said apparatus comprising:
(a) groove forming apparatus configured to form at least one groove in the web;
(b) securing apparatus configured to secure the stretchable material to the web while the web is in the grooved configuration such that, at the groove, a facing portion of the stretchable material is spaced from the continuously conveyed web and is in facing relationship with the continuously conveyed web; and
(c) urging apparatus configured to urge the facing portion of the stretchable material into the groove of the continuously conveyed web and thereby stretching the stretchable material, and securing the stretchable material to the continuously conveyed web in the groove while the facing portion of the stretchable material is in the stretched condition.

29. Apparatus as in claim 28, said groove forming apparatus comprising a forming plow, and first and second pressing rolls on opposing sides thereof.

30. Apparatus as in claim 29, said forming plow configured to form the groove such that the groove has a depth from about 2 centimeters to about 10 centimeters.

31. Apparatus as in claim 28, said securing apparatus comprising an applicator roll, said applicator roll configured to secure the stretchable material to the web in cooperation with respective first and second pressing rolls.

32. Apparatus as in claim 31, said first and second pressing rolls comprising first and second ultrasonic horns, said applicator roll comprising an ultrasonic anvil roll, said ultrasonic horns and ultrasonic anvil, in combination, configured to secure the stretchable material to the web.

33. Apparatus as in claim 28, including a knife roll, said knife roll configured to cut the stretchable material into discrete lengths before the stretchable material is secured to the web.

34. Apparatus as in claim 28, said urging apparatus comprising a push roll, said push roll, in combination with third and fourth pressing rolls, intermittently forcing the facing portion of the stretchable material into the groove and into physical contact with the web.

35. Apparatus as in claim 34, said push roll comprising an ultrasonic anvil having two opposing surfaces oriented at an angle of between about 45 degrees and about 60 degrees with respect to a plane defined by the stretchable material before the stretchable material is acted upon by said push roll, said opposing surfaces cooperating with respective ultrasonic horns to thereby secure at least part of the facing portion of the stretchable material to the web.

36. Apparatus as in claim 28, including a print roll configured to apply adhesive to the web, such that the web and stretchable material are secured adhesively to each other.

37. Apparatus as in claim 28, including a spray nozzle configured to apply adhesive to the web, such that the web and stretchable material are secured adhesively to each other.

38. Apparatus as in claim 28, including a spray nozzle configured to apply adhesive to the stretchable material.

39. Apparatus as in claim 28, the stretchable material having a substantially continuous length when applied to the web.

40. Apparatus as in claim 28, said groove forming apparatus comprising a vacuum roll, said vacuum roll having at least one ridge, and a valley, extending about the circumference of said vacuum roll, and vacuum ports located in said valley of said vacuum roll, the groove in the web being formed by applying vacuum at said vacuum ports.

41. Apparatus as in claim 40, said securing apparatus comprising a nip roll, said nip roll in combination with said vacuum roll forming a nip, the combination of said nip roll and said vacuum roll configured to secure the stretchable material to the continuously conveyed web, a facing portion of the stretchable material remaining displaced from the continuously conveyed web.

42. Apparatus as in claim 40, said urging apparatus comprising a mating roll having a ridge cooperating with the valley on the vacuum roll, the ridge on said mating roll forcing the stretchable material into the groove in the web to thereby effect securing the stretchable material and the web in surface-to-surface contacting relationship to each other.

43. Apparatus as in claim 42, said mating roll configured to adhesively secure the stretchable material and the web across substantially the entirety of the surface-to-surface relationship of the respective contacting surfaces.

44. Apparatus as in claim 28, said groove forming apparatus configured to form at least two grooves in the web.

45. Apparatus for fabricating a composite web having a length and transverse stretch, said apparatus comprising:
(a) groove forming apparatus forming a groove in a first web of material having a reference surface, the groove being displaced from the reference surface;

(b) securing apparatus securing a second web of stretchable material to the first web at first and second adjacent portions of the first web on opposing sides of the groove while maintaining the groove in the first web such that, at the groove, a facing portion of the second web is spaced from the first web and is in facing relationship with the first web; and (c) urging apparatus urging the facing portion of the second web into the groove and thereby stretching the second web, and securing the second web to the first web in the groove while the facing portion of the second web is in the stretched condition.

46. Apparatus as in claim 45, the securing apparatus securing the second web to the first web on opposing sides of the groove while the second web is in a relaxed, substantially unstretched condition.

* * * * *